United States Patent
Cully

(10) Patent No.: US 9,393,026 B2
(45) Date of Patent: Jul. 19, 2016

(54) VESSEL COMPRESSION DEVICES AND METHODS

(71) Applicant: W. L. Gore & Associates, Inc., Newark, DE (US)

(72) Inventor: Edward H. Cully, Flagstaff, AZ (US)

(73) Assignee: W. L. GORE & ASSOCIATES, INC., Newark (DE)

(*) Notice: Subject to any disclaimer, the term of this patent is extended or adjusted under 35 U.S.C. 154(b) by 140 days.

(21) Appl. No.: 13/869,410

(22) Filed: Apr. 24, 2013

(65) Prior Publication Data

US 2013/0289614 A1 Oct. 31, 2013

Related U.S. Application Data

(60) Provisional application No. 61/638,422, filed on Apr. 25, 2012.

(51) Int. Cl.
*A61B 17/00* (2006.01)
*A61B 17/132* (2006.01)

(52) U.S. Cl.
CPC ......... *A61B 17/1322* (2013.01); *A61B 17/1325* (2013.01)

(58) Field of Classification Search
CPC ............. A61H 11/00; A61H 2011/005; A61B 17/1322; A61B 17/132; A61B 17/1325; A61B 17/1355
USPC .......................................... 606/201, 203, 204
See application file for complete search history.

(56) References Cited

U.S. PATENT DOCUMENTS

| | | | |
|---|---|---|---|
| 3,050,064 A * | 8/1962 | Moore | A61B 17/1325 606/203 |
| 3,095,873 A | 7/1963 | Edmunds | |
| 4,858,596 A | 8/1989 | Kolstedt et al. | |
| 5,514,079 A | 5/1996 | Dillon | |
| 5,634,889 A | 6/1997 | Gardner et al. | |
| 7,344,548 B2 | 3/2008 | Toyota et al. | |
| 8,079,969 B2 | 12/2011 | Rousso et al. | |
| 8,100,842 B2 | 1/2012 | Rousso | |
| 8,105,252 B2 | 1/2012 | Rousso | |
| 2005/0113866 A1* | 5/2005 | Heinz | A61B 17/1327 606/203 |
| 2005/0125025 A1* | 6/2005 | Rioux | A61B 17/0057 606/201 |
| 2007/0173886 A1* | 7/2007 | Rousso | A61H 11/02 606/203 |
| 2007/0191881 A1* | 8/2007 | Amisar | A61B 17/1355 606/203 |
| 2008/0015630 A1* | 1/2008 | Rousso | A61H 9/0078 606/202 |
| 2008/0097268 A1* | 4/2008 | Rousso | A61H 11/02 602/13 |

(Continued)

FOREIGN PATENT DOCUMENTS

CN 2010/05962 1/2008

OTHER PUBLICATIONS

Rus, R. R. Effect of intermittent compression of upper arm veins on forearm vessels in patients with end-stage renal disease; Hemodialysis International, Jul. 2005, vol. 9 Issue 3, p. 275-280.

*Primary Examiner* — Tuan V Nguyen
*Assistant Examiner* — Kevin Everage

(57) ABSTRACT

Embodiments of the present disclosure comprise compression devices and methods for applying intermittent and localized vessel compression. The compression devices and methods as described herein can improve fistula circuit maturity rates by promoting vein dilation. An aspect of the present disclosure is directed toward depressor designs actuated using actuator wire(s).

20 Claims, 4 Drawing Sheets

(56) References Cited

U.S. PATENT DOCUMENTS

| | | |
|---|---|---|
| 2008/0177159 A1 | 7/2008 | Gavriely |
| 2009/0234261 A1 | 9/2009 | Singh |
| 2009/0234265 A1 | 9/2009 | Reid et al. |
| 2009/0281565 A1* | 11/2009 | McNeese ............ A61B 17/1325 606/201 |
| 2009/0287243 A1 | 11/2009 | Greennberg |
| 2009/0299239 A1* | 12/2009 | Meyer .................. A61H 9/0078 601/149 |
| 2010/0010402 A1* | 1/2010 | Porter, Jr. ................ A61H 7/001 601/134 |
| 2011/0208067 A1 | 8/2011 | Edman et al. |
| 2011/0208097 A1 | 8/2011 | Farese et al. |
| 2012/0150215 A1* | 6/2012 | Donald .............. A61B 17/1327 606/203 |
| 2013/0304112 A1* | 11/2013 | Ting ....................... A61B 5/021 606/203 |

* cited by examiner

VESSEL COMPRESSION DEVICES AND METHODS

CROSS REFERENCE TO RELATED APPLICATIONS

This application claims the priority benefit under U.S.C. §119(e) to U.S. Provisional Application No. 61/638,422 filed on Apr. 25, 2012 and the content of which is incorporated herein in its entirety.

BACKGROUND

1. Field

The present disclosure relates to vessel compression devices and methods, for example to automatic tourniquet devices and methods for applying intermittent and localized vessel compression.

2. Discussion of the Related Art

Vascular access is of particular importance for patients on hemodialysis. Arteriovenous ("AV") fistulas are generally considered an acceptable mode of vascular access for chronic hemodialysis. Primary and long-term success can depend, in part, on the state of the arteries and veins at the time of fistula creation.

One factor believed to be determinative of AV fistula success or failure is the diameter of the vein at the site of fistula creation. Clinical studies have suggested that daily, prolonged intermittent compression of a vein with a tourniquet can increase the diameter of the vein in a region upstream to the compression site, and thus increase the likelihood of successful fistula maturation.

Accordingly, there is a need for a compression device that applies intermittent compression to a localized area for purposes of improving the maturation rates of fistulas and reducing the incidence of fistula failure, while minimizing cost and patient discomfort.

SUMMARY

The present disclosure is directed toward devices and methods for use in connection with localized vessel compression, for example automatic tourniquets. Disclosed compression devices can be operable for applying intermittent and localized vessel compression and can improve fistula circuit maturity rates by promoting vein dilation.

Embodiments described herein are directed toward a compression device comprising at least one actuator wire coupled to the support piece and a depressor such that when an electrical current is applied to the actuator wire, the depressor is forced in a direction that compresses the target vessel. Methods of using the same are also described herein. The use of actuator wire(s) can be beneficial because noise generated during operation can be negligible, and the wires can be lightweight, thereby enhancing the user's experience and the portability of the device.

Other embodiments described herein are directed toward compression device designs that are adjustable to accommodate for anatomical differences between users, e.g., the depressor can be length adjustable and/or all or a portion of the depressor in direct contact with a tissue, such as the skin, can be interchangeable.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION

Figure 1A:
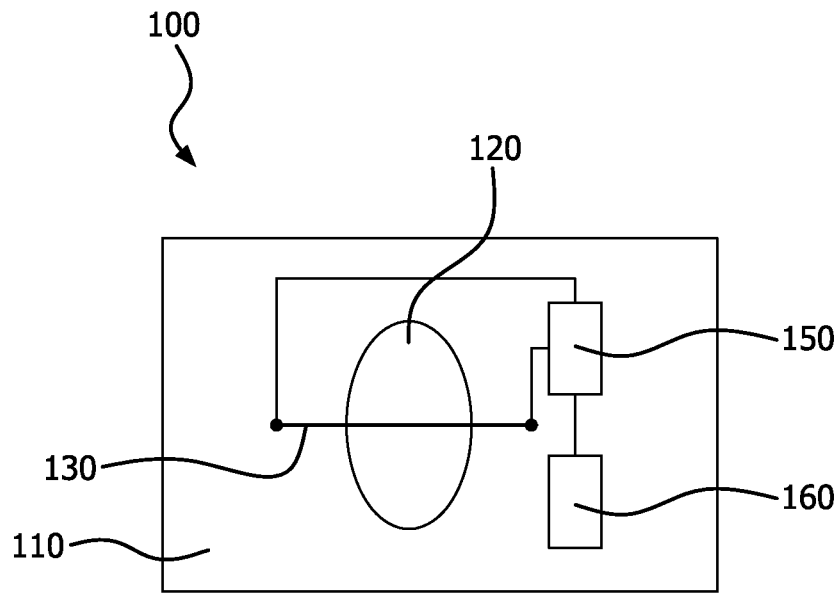
FIGS. 1A and 1B illustrate schematic views of a tourniquet device.

Persons skilled in the art will readily appreciate that various aspects of the present disclosure can be realized by any number of methods and apparatuses capable of performing the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting.

Although the present disclosure can be described in connection with various principles and beliefs, the present disclosure should not be bound by theory. For example, the present disclosure may be described herein in connection with an automatic tourniquet in the context of hemodialysis vessel. However, the present disclosure can be applied toward any localized vessel compression devices or methods of similar structure and/or function. Furthermore, the present disclosure can be applied in nonvascular applications and even non-biologic and/or non-medical applications.

The terms "downstream" and "upstream," when used herein in relation to a users vasculature, refer to the direction of blood flow and the direction opposite that of blood flow, respectively. In the venous system, "upstream" refers to the direction further from the heart, while "downstream" refers to the direction closer to the heart.

The term "vessel", as used herein, comprises any conduit and includes an artery or vein.

The term "compression," as used herein, comprises a reduction in volume or the constriction of an object, e.g., a vessel, by applying pressure on a surface, e.g., a tissue. Embodiments described herein are capable of applying localized and/or intermittent compression.

The term "user," as used herein, comprises a wearer and/or an operator of the various illustrated embodiments and can include, for example, a patient and/or a clinician.

The present disclosure is directed toward devices and methods for use in connection with localized vessel compression, for example automatic tourniquets. Disclosed compression devices can be operable for applying intermittent and localized vessel compression and can improve fistula circuit maturity rates by promoting vessel dilation. Compression devices as described herein include tourniquet devices, which can be automatic.

Compression devices and methods, in accordance with the present disclosure, comprise one or more depressors, which facilitate the application of a compressive force to a vessel. In accordance with some embodiments, a compression device is operable to compress a vessel through the application of a current in one or more actuator wires. When a current is applied, the temperature of the actuator wire increases, and the wire shortens in length. When the wire cools, the wire will generally lengthen if a bias force is present. Described embodiments are capable of actuating a depressor upon the shortening of the wire, thereby compressing the user's tissue over a small area and restricting the flow of a target vessel. As the wire cools, the elasticity of the tissue can provide a bias force to lengthen the wire, allowing the depressor to retract. Elasticity of a tissue is the ability of the tissue, e.g., skin, to return to its normal state after the removal of a force, such as a force that deforms, compresses, and/or stretches the tissue. In some embodiments, a spring can also be used to provide a bias force.

As the structural component that engages the tissue to compress the target vessel, in accordance with various embodiments, the depressor can be adjustable to adapt to the anatomical differences between users. For example, the depressor can be interchangeable, length adjustable, and/or comprise a focal end that is interchangeable. In accordance with embodiments, compression device designs can also be portable and minimally obtrusive.

Figure 1B:
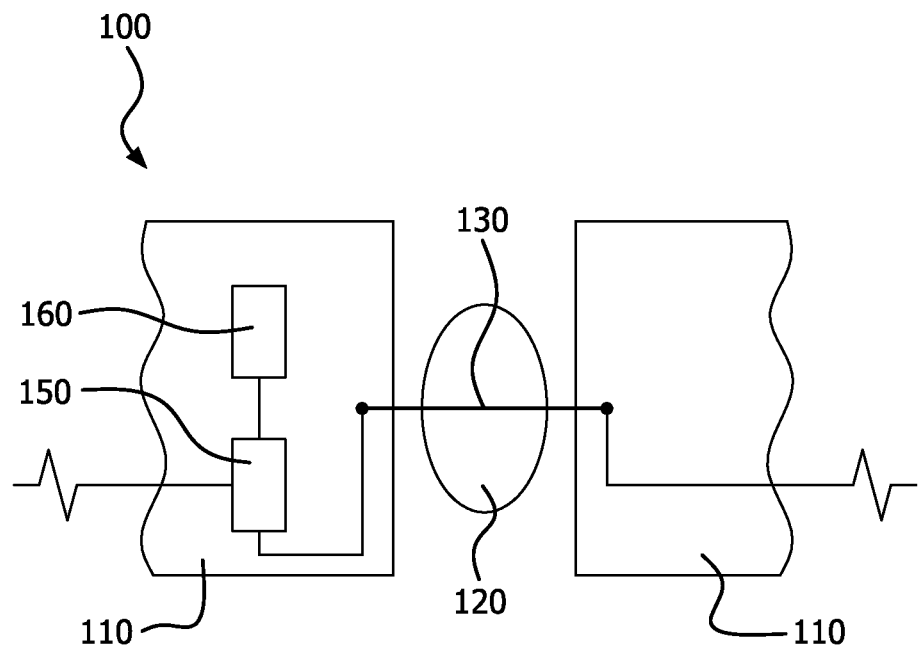

With reference to FIGS. 1A and 1B, in accordance with various embodiments, a compression device 100 comprises a support piece 110, such as a cuff, a depressor 120, and at least one actuator wire 130 coupled to support piece 110 and depressor 120 such that when an electrical current is applied to actuator wire 130, depressor 120 is forced in a downward direction. Compression device 100 can additionally comprise a power supply 150 connected to actuator wire(s) 130, such as a battery or other portable power supply device, or be configured to connect to an external power supply. In some embodiments, compression device 100 can also comprise control electronics 160.

Figure 2A:
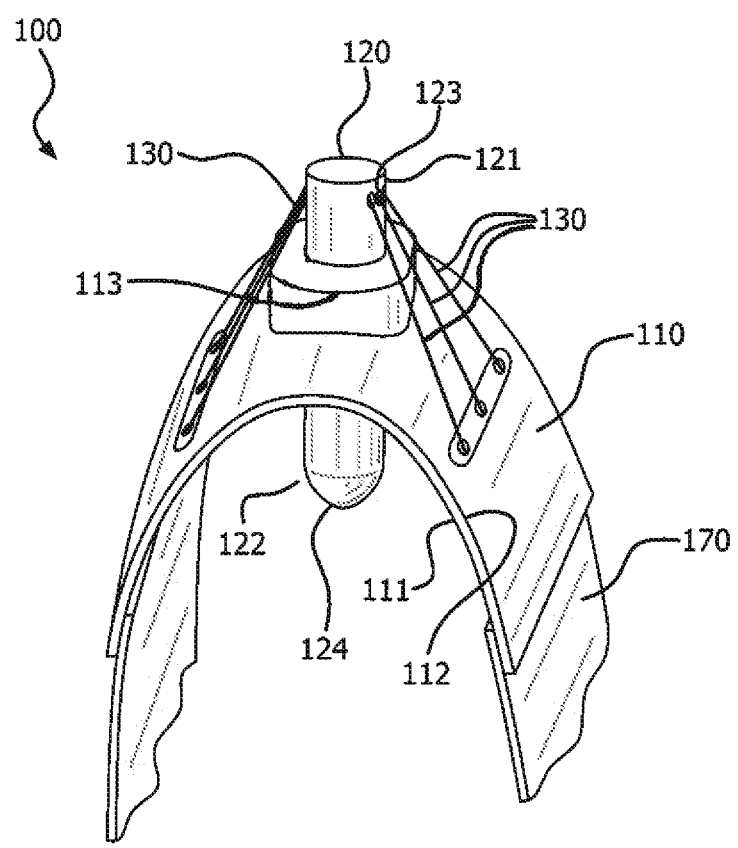
FIG. 2A illustrates a perspective view of an embodiment of a tourniquet device.
Figure 2B:
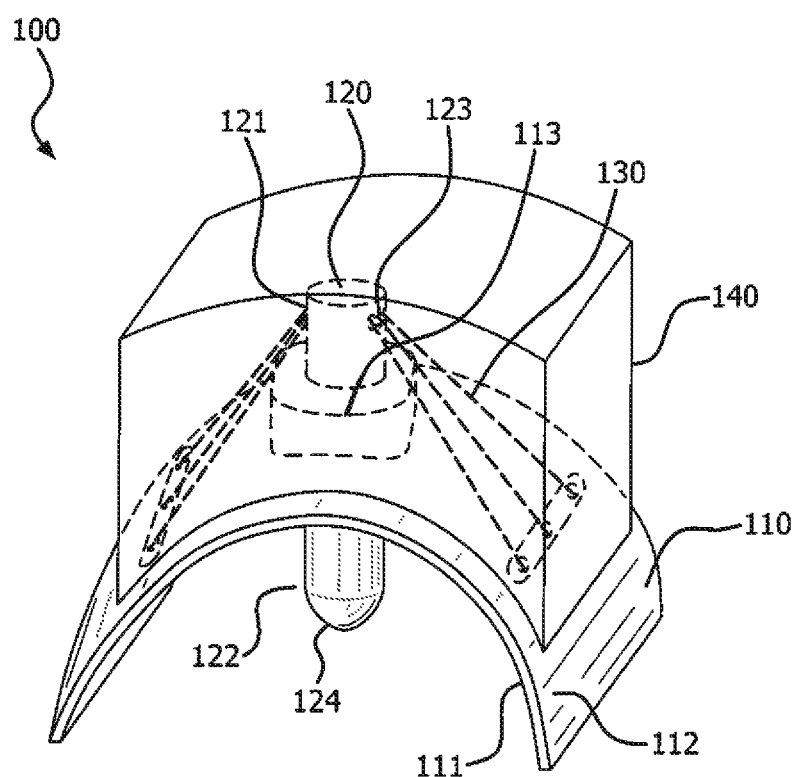
FIGS. 2B and 2C illustrate a perspective view of an embodiment of a tourniquet device having a cover.
Figure 2C:
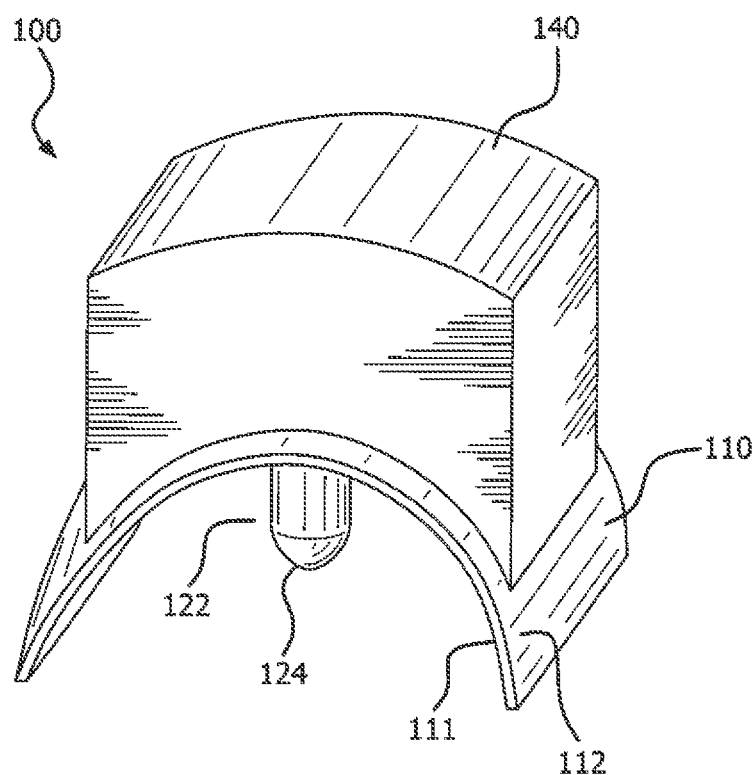

Now with reference to FIGS. 2A to 2C, support piece 110 can comprise a structural component for securing actuator wire(s) 130 and facilitating movement of depressor 120 in a downward direction. In an embodiment, support piece 110 comprises one or more of a plate, band, strip, or the like having an interior face 111 and an exterior face 112. Although not required, interior face 111 can be generally contoured to lie along a tissue, e.g., the surface of the skin, at the site of vessel compression. By way of example, if compression device 100 is intended to compress a target vessel on the forearm or upper arm, support piece 110 can comprise a band having an arc-like or curved configuration, such as a cuff.

In an embodiment, support piece 110 can comprise a compression region 113. Compression region 113 can comprise an opening or a deformable region that allows for the depressor 120 to actuate and can also serve to stabilize the movement of depressor 120. An opening can comprise an appropriately sized aperture through support piece 110 or a space between two or more elements of support piece 110.

Support piece 110 can comprise any material suitable for its function. For example, support piece 110 can comprise a material that is sufficiently rigid such that when actuator wire(s) 130 shortens, support piece 110 is not deformed. For purposes of portability, the material can be low density or a lightweight material, such as a lightweight metal or metal alloy, e.g., support piece 110 comprising aluminum or titanium. Other lightweight materials include a carbon fiber laminate, a hard plastic polymer, and/or the like.

Notwithstanding the rigidity, support piece 110 can also be sufficiently bendable to facilitate approximately molding to the general contour of the tissue surface. Additionally, for purposes of comfort, the interior face 111 of support piece 110 can be lined with a soft or shock absorbent material, such as a knit or woven fabric or foam strip, a wicking material, etc. Interior face 111 can also be lined with a slip resistant material.

In an embodiment, actuator wire(s) 130 can comprise any wire or strip that shortens in length when an electrical current is applied. For example, actuator wire 130 can comprise a shape memory alloy, such as Flexinol®. As stated above, the shortening of actuator wire(s) 130 forces depressor 120 in a downward direction, and the lengthening of actuator wire(s) 130 permits depressor 120 to retract.

In various embodiments, any number of actuator wires 130 is contemplated, such as one, two, three, four, five, or more. The number of actuator wires 130 can depend on the amount of downward force required to compress a target vessel for purposes of upstream vessel dilation. The use of one or more actuator wires 130 can be beneficial because noise generated during operation can be negligible, and the wires 130 can be lightweight, thereby enhancing the user's experience and the portability of device 100.

In an embodiment, depressor 120 comprises any structural component shaped in a manner to apply a localized compression to a desired area and to engage actuator wire 130 such that when actuator wire 130 shortens, depressor 120 translates in a downward direction in order to compress a target vessel. For example, depressor 120 can comprise a sufficiently rigid component having an upper portion 121 and a base portion 122. Upper portion 121 engages with actuator wire(s) 130 and base portion 122 comprises a focal end 124 that engages a tissue. Focal end 124 contacts and presses down on the tissue.

Focal end 124 can comprise a surface profile suitable for localized compression of the tissue, e.g., by contacting the surface of the skin, to compress a target vessel. For example, focal end 124 dimensions can be from about 0.5 $cm^2$ up to about 4 $cm^2$ or more. Focal end 124 can comprise rounded edges or a surface texture or covering that helps minimize or prevent tissue irritation as it presses downward on the tissue.

In order to actuate depressor 120, both ends of actuator wire 130 can be attached to support piece 110 and strung over or through upper portion 121. Alternatively, one end of actuator wire 130 can be attached to upper portion 121 and the other to support piece 110. Accordingly, upper portion 121 can comprise a structural feature or attachment device that serves to restrain actuator wire(s) 130 in a position for actuating depressor 120. For example, in an embodiment, where actuator wire(s) 130 are strung over or through upper portion 121, upper portion 121 of depressor 120 can comprise a channel 123 across or through, along which actuator wire(s) 130 pass. Any restraint or attachment mechanism can be utilized including, but not limited to a screw, pin, adhesive, or the like.

Depressor 120 can be adjustable in order to be adapted to anatomical differences between users. For example, depressor 120 can be length adjustable. Similarly, the surface profile of the focal end 124 can be interchangeable. In one embodiment, depressor 120 can comprise an interchangeable base portion 122 in order to change the dimensions or surface profile of the focal end 124. Base portion 122 or upper portion 121 can also be interchanged for purposes of changing the length. Other configurations can comprise adding extension inserts. Components of the depressor can be threaded and/or telescoping to allow convenient length adjustability based on individual user anatomy.

In order to secure tourniquet 100 to the user, compression device 100 can comprise a securing mechanism, e.g., a strap 170. For example, strap 170 can attach to support piece 110 for purposes of securing compression device 100 to the user. Strap 170 can comprise a strip of pliable fabric and fastener such as a hook and loop fastener (e.g., Velcro®), buttons, buckles, or the like. Embodiments can comprise an adhesive strip attached to interior face 111 or across exterior face 112 in order to secure tourniquet 100 to the user. Embodiments can further comprise mechanisms that make it difficult for the user, e.g., the patient, to remove or to operate him or herself. Such mechanisms can include, for example, slip resistant linings; a lock and key fastening device, which can utilize cover 140 (described below); and/or control electronics 160 capable of providing password protected access to control the operation parameters and/or power the device on and off.

To act as a shield between the user and the exposed sections of actuator wire 130, compression device 100 can comprise cover 140 that is situated over at least the exposed sections of actuator wire(s) 130. Cover 140 can comprise a sleeve that fits around actuator wire 130, or a dome-like structure that sits over and couples to support piece 110, as illustrated in FIGS. 2B and 2C; yet various other cover embodiments are contemplated.

As stated above, actuator wire 130 shortens by applying an electrical current through actuator wire(s) 130. When the current through wire 130 ceases, wire 130 cools and will lengthen if a bias force is present. In some embodiments, the elasticity of the user's own tissue can apply a bias force. In some embodiments, compression device 100 can comprise a spring mechanism coupled to depressor 120 or actuator wire(s) 130 for applying a bias force in order to retract depressor 120 at the end of a compression cycle.

In order to power the device, compression device 100 can further comprise a power supply 150, such as a battery. Power supply 150 can be mounted on support piece 110 or be a separate component electrically connected to actuator wire(s) 130. Power supply 150 can be rechargeable, but can also be single-use. Power supply 150 can comprise a battery, such as an alkaline, nickel-metal hydride, lithium-ion, lithium-polymer, and/or other battery configurations suitable for applying a current to actuator wire(s) 130 and powering control electronics 160 and the like. Moreover, power supply 150 can comprise any suitable chemistry, form factor, voltage, and/or capacity suitable to provide power to compression device 100. Power supply 150 can be decoupled from compression device 100, for example, to facilitate recharging or be capable of connecting to an external power supply without decoupling. Alternatively, compression device 100 can be powered by an external power supply via a power cord.

In an embodiment, compression device 100 can be configured such that the downward force applied to the depressor 120 by actuator wire 130 is intermittent. For example, compression device 100 can comprise control electronics 160 in order to apply intermittently an electrical current to actuator wire 130. Compression device 100 can further be programmable, such as to control the rate of a depressor 120 actuation, the duration of a depressor 120 actuation cycle, and the amount of time for a depressor 120 actuation session. As such, compression device 100 can comprise inputs and a display, for example, as part of control electronics 160.

Accordingly, control electronics 160 and/or an associated software subsystem comprise components capable of controlling the operation of compression device 100, namely the application of current to actuator wire(s) 130. For example, control electronics 160 can comprise integrated circuits, discrete electrical components, printed circuit boards, the like, and combinations of the same. Control electronics 160 can further comprise clocks or other timing circuitry. Control electronics 160 can also comprise data logging circuitry, for example volatile or non-volatile memories and the like, to store data, such as data regarding operation and functioning of compression device 100. Moreover, a software subsystem can be pre-programmed and communicate with control electronics 160 in order to adjust operation parameters of compression device 100, for example the rate of a depressor 120 actuation, the duration of a depressor 120 actuation cycle, and the amount of time for a depressor 120 actuation session. Control electronics 160 can be capable of receiving instructions from an input and providing feedback to a user via a display or other output device.

Control electronics 160 can be capable of storing data related to compression device 100. For example, control electronics 160 can record the duration that the compression device 100 is active, the number of compression cycles performed, the parameters under which the cycles where performed, and so forth. Moreover, control electronics 160 can further comprise circuitry for enabling data storage in control electronics 160 to be retrieved for analysis, deleted, compacted, encrypted, wirelessly transmitted, and/or the like.

Control electronics 160 can monitor the pressure applied by depressor 120 when depressor 120 is being forced downward by actuator wire(s) 130. For example, control electronics 160 can monitor the current drawn by wire and calculate the applied pressure. Alternatively, a pressure sensor can detect the applied pressure and report this value to control electronics 160 and/or an associated software subsystem.

Control electronics 160 can monitor the operating current, operating voltage, and/or leakage current to ensure proper and safe function of compression device 100.

To control the operation of compression device 100, control electronics 160 can comprise inputs. Inputs can allow a user to turn compression device 100 on and off. Inputs can also allow a user to adjust operation parameters of compression device 100. Operation parameters for compression device 100 can include, for example, the rate of a depressor 120 actuation, the duration of a depressor 120 actuation cycle, and the amount of time for a depressor 120 actuation session, and/or the like. Further, inputs can allow retrieval of data, such as system usage records.

In an embodiment, inputs comprise electronic buttons, switches, wireless receivers, or similar devices. In other embodiments, inputs can comprise a communications port, for example a Universal Serial Bus (USB) port. Further, inputs can comprise variable pressure control switches with corresponding indicator lights. Inputs can also comprise variable speed control switches with corresponding indicator lights, on/off switches, pressure switches, click wheels, trackballs, d-pads, and/or the like. Moreover, inputs can comprise any suitable components capable of allowing a user to control operation of compression device 100.

In accordance with further embodiments, compression device 100 can comprise a display capable of presenting information and/or feedback to a user. In an embodiment, the display comprises a liquid crystal display (LCD). In other embodiments, the display comprises light emitting diodes (LEDs). The display can comprise visual and audio communication devices such as speakers, alarms, and/or other similar monitoring and/or feedback components. Moreover, the display can also comprise audible or tactile feedback components.

In accordance with an embodiment, a method of use can comprise the steps of providing compression device 100 as described herein, locating depressor 120 over a vessel, and applying a current to actuator wire(s) 130, thereby forcing depressor 120 downward to compress the vessel. The site of vessel compression can be downstream from a fistula site to facilitate fistula maturation. Additional steps of the method can comprise adjusting at least one of the rate of depressor 120 actuation, the duration of depressor 120 actuation cycle, and the amount of time for depressor 120 actuation session.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A device comprising:
    a support piece having a compression region and a strap releasaby attached to the support piece;
    a depressor having a cylindrical upper portion disposed within an aperture in the compression region and a base portion coupled to the upper portion, wherein the base portion comprises a focal end having a surface profile; and
    an actuator wire coupled to the support piece and the upper portion of the depressor such that when an electrical current is applied to the actuator wire, the wire changes in length forcing the depressor to compress a vessel.

2. The device of claim 1 further comprising a cover that sits over at least an exposed portion of the actuator wire and attaches to the support piece.

3. The device of claim 2, wherein the cover is releasably attached.

4. The device of claim 1, further comprising a plurality of actuator wires coupled to the support piece and the upper portion of the depressor such that when the electrical current is applied to the actuator wire, the depressor is forced downward to compress the vessel.

5. The device of claim 1, wherein the support piece is bendable.

6. The device of claim 1, wherein the support piece comprises a curved shape.

7. The device of claim 6, wherein the curved shape of the support piece is capable of fitting to an arm.

8. The device of claim 1, wherein the depressor comprises an adjustable length.

9. The device of claim 1, wherein the base portion is interchangeable.

10. The device of claim 1, wherein the compression region comprises an opening and the depressor extends through the opening.

11. The device of claim 1, further comprising a power supply electrically connected to actuator wires.

12. The device of claim 1, wherein a downward force is applied intermittently.

13. The device of claim 1, further comprising control electronics to program or adjust at least one of a rate of depressor actuation, duration of depressor actuation cycle, and amount of time for a depressor actuation session.

14. The device of claim 1, wherein the base portion comprises a surface profile of sufficient surface area to apply a localized compression to compress a target vessel.

15. The device of claim 1, further comprising a focal end less than 2 $cm^2$, wherein the focal end is located at an end of the base portion.

16. The device of claim 1, wherein the surface profile of the focal end comprises a rounded edge.

17. The device of claim 1, wherein the upper portion comprises a cavity through which the actuator wire passes through.

18. A method comprising:
    locating a depressor over a target vessel, the depressor having a cylindrical upper portion disposed within an aperture in a compression region and a base portion coupled to the upper portion, wherein the base portion comprises a focal end having a surface profile; and
    applying a current to an actuator wire coupled to the support piece and the upper portion of the depressor, the current causing the wire to change in length such that the depressor is forced to compress the target vessel.

19. The method of claim 18, wherein a site of target vessel compression is downstream from a fistula site.

20. The method of claim 18, adjusting at least one of the rate of a depressor actuation, duration of a depressor actuation cycle, and amount of time for a depressor actuation session.

* * * * *